United States Patent
Melamed

(10) Patent No.: US 11,219,629 B2
(45) Date of Patent: Jan. 11, 2022

(54) ANESTHETIC PHARMACEUTICAL COMPOSITION, SYSTEM AND METHOD

(71) Applicant: Hooman M. Melamed, Beverly Hills, CA (US)

(72) Inventor: Hooman M. Melamed, Beverly Hills, CA (US)

(*) Notice: Subject to any disclaimer, the term of this patent is extended or adjusted under 35 U.S.C. 154(b) by 70 days.

(21) Appl. No.: 16/656,466

(22) Filed: Oct. 17, 2019

(65) Prior Publication Data

US 2021/0113591 A1 Apr. 22, 2021

(51) Int. Cl.
| | | |
|---|---|---|
| *A61K 31/415* | (2006.01) | |
| *A61K 31/573* | (2006.01) | |
| *A61K 31/197* | (2006.01) | |
| *A61K 31/167* | (2006.01) | |
| *A61K 9/00* | (2006.01) | |
| *A61K 31/445* | (2006.01) | |
| *A61K 31/135* | (2006.01) | |
| *A61K 31/407* | (2006.01) | |

(52) U.S. Cl.
CPC .......... *A61K 31/573* (2013.01); *A61K 9/0019* (2013.01); *A61K 31/135* (2013.01); *A61K 31/167* (2013.01); *A61K 31/197* (2013.01); *A61K 31/407* (2013.01); *A61K 31/415* (2013.01); *A61K 31/445* (2013.01)

(58) Field of Classification Search
CPC .. A61K 31/197; A61K 31/135; A61K 31/167; A61K 31/415; C07C 217/52; C07C 229/08; C07C 233/88; C07D 231/12

USPC ............ 514/406, 547, 561, 630; 548/375.1; 562/553; 564/219, 307

See application file for complete search history.

(56) References Cited

U.S. PATENT DOCUMENTS

| | | | |
|---|---|---|---|
| 4,783,465 A | 11/1988 | Sunshine et al. | |
| 6,007,841 A | 12/1999 | Caruso | |
| 10,287,334 B2 | 5/2019 | Khanna et al. | |
| 2019/0029988 A1* | 1/2019 | Poulsen | .................. A61P 43/00 |

* cited by examiner

*Primary Examiner* — Jeffrey H Murray
(74) *Attorney, Agent, or Firm* — Omni Legal Group; Omid E. Khalifeh; Lara A. Petersen

(57) ABSTRACT

An anesthetic pharmaceutical composition, system and method is provided. The anesthetic pharmaceutical composition comprises an intraoperative local injection and one or more postoperative medications. The intraoperative local injection is long-acting and comprises at least one local anesthetic agent, such as ropivacaine; ketorolac; and at least one steroid, such as dexamethasone. The one or more postoperative medications comprise an atypical opioid agonist, such as tramadol; a non-steroidal anti-inflammatory drug, such as a cyclooxygenase-2 inhibitor; a gamma-aminobutyric acid analogue, such as pregabalin; and acetaminophen. The method comprises the steps of commencing a surgical procedure involving one or more incision sites; injecting an intraoperative local injection at the one or more incision sites; performing and completing the surgical procedure; and administering one or more postoperative medications.

8 Claims, 1 Drawing Sheet

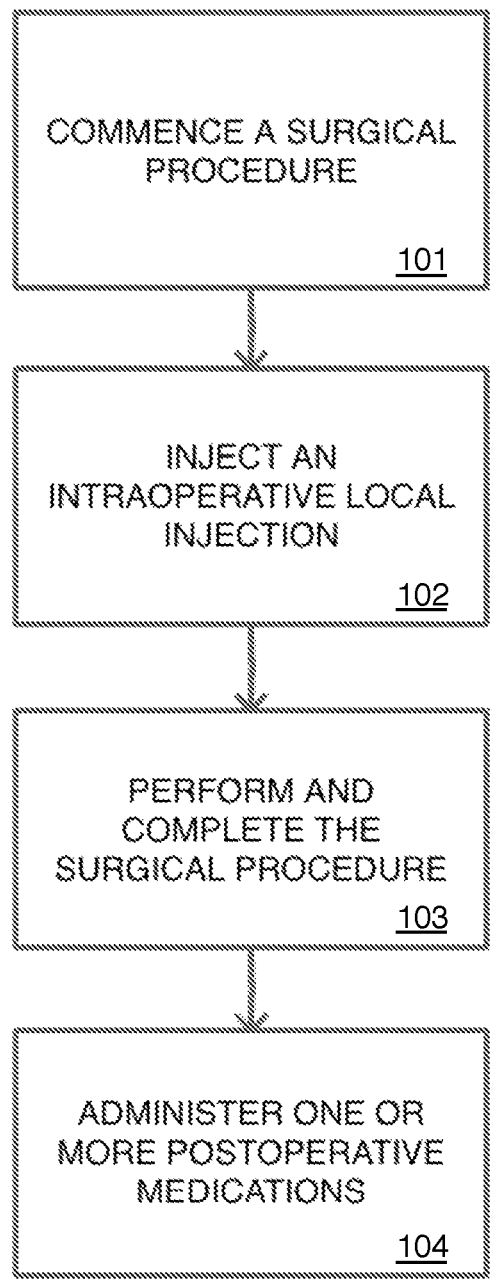

ANESTHETIC PHARMACEUTICAL COMPOSITION, SYSTEM AND METHOD

GOVERNMENT CONTRACT

Not applicable.

CROSS-REFERENCE TO RELATED APPLICATIONS

Not applicable.

STATEMENT RE. FEDERALLY SPONSORED RESEARCH/DEVELOPMENT

Not applicable.

COPYRIGHT & TRADEMARK NOTICES

A portion of the disclosure of this patent document may contain material which is subject to copyright protection. This patent document may show and/or describe matter which is or may become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

The disclosed subject matter relates generally to anesthetic pharmaceutical compositions and, more particularly, to an anesthetic pharmaceutical composition, system and method effective in mitigating surgical pain and discomfort while reducing the risk of opioid abuse or addiction.

BACKGROUND

The term opioid refers to all compounds that bind to opiate receptors in the brain, including naturally occurring opiates, and synthetic and semi-synthetic opioids, which mimic the effects of endogenous opiates. The term narcotic, on the other hand, is a legal designation that refers to opioids and other drugs that dull the senses and relieve pain. Examples include OxyContin, Vicodin, codeine, morphine, methadone, and fentanyl. Opioids may be administered orally, transdermally, intravenously, perineurally, sublingually, or transcutaenously in order to deliver its effects. Opioids act by binding to specific proteins, called opioid receptors, which are widely distributed and are involved in pain modulation in both the central and peripheral nervous systems. When opioids binds to these receptors, analgesia, or loss of pain sensation, results.

Pain is defined by the International Association for the Study of Pain (IASP) as "an unpleasant sensory and emotional experience associated with actual or potential tissue damage or described in terms of such damage." Nociception is the process through which potentially damaging stimuli are detected. The precise mechanisms of pain perception and transmission have not been fully elucidated. However, it is known that endogenous opioids, otherwise known as endorphins, bind G protein coupled opioid receptors, thereby activating pathways which inhibit the perception of pain. Additionally, monoamine neurotransmitters, serotonin and norepinephrine, have a role in the modulation of pain in that increased circulation of serotonin and norepinephrine, resulting from reuptake inhibitors, have been shown to reduce pain and functional impairment.

Along with the beneficial function of relieving pain, opioids carry a number of negative side effects. Studies have shown that opioids cause adverse events in several physiological systems. As one example, long-term opioid use can result in sleep-disordered breathing and other respiratory issues. Other examples include dizziness, nausea, vomiting, constipation, fractures, and hypothalamic-pituitary-adrenal dysregulation.

In addition to the foregoing, while opioids are generally safe when used for a limited time period, as prescribed, these substances have a high tendency for misuse. In particular, due to the resultant feeling of well-being or euphoria, individuals are prone to taking higher than prescribed doses, ingesting another's prescription, ingesting the drug to get high, or even overdosing. Indeed, every day, more than 130 people in the United States die from an opioid overdose. Additionally, the Centers for Disease Control and Prevention estimate that the economic burden of prescription opioid misuse alone is $78.5 billion per year.

To make matters worse, recent research has indicated that the use of narcotic pain medications trick the body into thinking it is experiencing more pain that in reality. After multiple weeks of opioid use, individuals become more sensitive to pain, thereby rendering the perception of pain worse. While opioids do provide pain relief by blocking pain, after extended use, the human body reacts by increasing the number of opioid receptors in order to bypass this blockage. Additionally, the more the body acclimates to exogenous opioids, its ability to create and use natural endorphins decreases, eventually causing a loss of the ability to endogenously reduce pain. In this way, the pain continues to increase, not due to the injury itself, but due to the opioids.

Due to the foregoing, there exists a need for non-narcotic anesthetic compounds for use in the treatment of postoperative pain and discomfort. More particularly, there remains a need for anesthetic compounds which effectively reduce pain without the potential concomitant abuse and addiction.

SUMMARY

The present disclosure is directed to anesthetic pharmaceutical compositions, systems and methods that alleviate surgical pain without significant risk for resultant narcotic addiction. More particularly, the pharmaceutical composition may provide antinociceptive as well as anti-inflammatory properties. In this manner, the composition may delay the onset of postoperative pain and reduce the intensity of intraoperative and postoperative pain.

For purposes of summarizing, certain aspects, advantages, and novel features have been described. It is to be understood that not all such advantages may be achieved in accordance with any one particular embodiment. Thus, the disclosed subject matter may be embodied or carried out in a manner that achieves or optimizes one advantage or group of advantages without achieving all advantages as may be taught or suggested.

In accordance with one embodiment, the pharmaceutical composition may comprise an intraoperative local injection, an atypical opioid agonist, a non-steroidal anti-inflammatory drug, a gamma-aminobutyric acid (GABA) analogue, and acetaminophen. The intraoperative local injection may be long-acting and may further comprise a local anesthetic agent, ketorolac, and at least one steroid. In preferred embodiments, the local anesthetic agent may comprise ropivacaine. The intraoperative local injection may numb a specific area of the body and that area may correspond to an area of surgical operation. In other embodiments, the intraoperative local injection may numb a region of the body or even, the entire body. Moreover, the intraoperative local injection may reduce narcotic utilization during the initial time period following the operation.

According to certain embodiments, the at least one steroid may be dexamethasone. A person of ordinary skill in the art will recognize that dexamethasone is an adjuvant agent in that it modifies the effects of other pharmacological or immunological compounds. Indeed, dexamethasone may reduce inflammation at the area of surgical operation, extend the analgesic duration of the intraoperative local injection, among other actions. In other embodiments, the at least one steroid may be dexmedetomidine or another steroid known to those skilled in the art.

Ropivacaine may block nerve impulse transmission in the targeted tissue or region of the body for a period of 30 minutes to 12 hours or more. While, as mentioned above, in some embodiments, ropivacaine may be replaced or supplemented with another long-acting local anesthetic agent, one of ordinary skill in the art will recognize that ropivacaine may be desirable, in part, because it may provide a greater degree of motor sensory differentiation. More particularly, ropivacaine may deaden certain nerve endings associated with the area of surgical operation while leaving other nerve endings fully functional. However, in certain embodiments, ropivacaine may be combined with or supplanted by another long-acting local anesthetic agent of the amino amide class or the amino ester class. For instance, the other long-acting local anesthetic agent may be bupivacaine, lidocaine, mepivacaine, tetracaine, procaine, benzocaine, or another compound.

The intraoperative local injection may also comprise ketorolac. One of ordinary skill in the art will understand that ketorolac is a nonsteroidal anti-inflammatory drug (NSAID) that reduces hormones that cause inflammation and pain in the body. In this manner, ketorolac may be used relief of short-term moderate to severe pain, including that which may be experienced post-operation. In alternate embodiments, ketorolac may be replaced or supplemented with another NSAID, such as naproxen, nabumetone, or etodolac.

Depending on the type of operation and the size of the incision site, the quantity of the intraoperative local injection may vary. For instance, 12 mL to 20 mL of ropivacaine, 1 mL to 3 mL of the at least one steroid, and 1 mL to 2 mL of ketorolac may be provided. In operations involving a large incision site, the maximum dose of the intraoperative local injection may be used. On the other hand, in operations involving a relatively smaller incision site, the minimum dose of the intraoperative local injection may be injected.

As stated above, the pharmaceutical compound may also comprise an atypical opioid agonist. The atypical opioid agonist, as compared to full opioid agonists, cause less opioid receptor activation. As a result, the atypical opioid agonist is less potent than full opioid agonists, such as fentanyl, codeine, hydrocodone, oxycodone, morphine, or methadone, and carries a lower potential for abuse. Nonetheless, the atypical opioid agonist may be a synthetic pain reliever and in this way, may stimulate opioid receptors in the brain, which regulate the transmission of pain sensation. In addition, the atypical opioid agonist may stimulate presynaptic release and inhibit reuptake of serotonin and norepinephrine in the brain, thereby having an antinociceptive effect. In some preferred embodiments, the atypical opioid agonist may be tramadol. In other embodiments, the atypical opioid agonist may be buprenorphine, butorphanol, pentazocine, or a full opioid agonist.

The non-steroidal anti-inflammatory drug (NSAID) of the present invention may be a cyclooxygenase-2 (COX-2) inhibitor. One of ordinary skill in the art will recognize that COX-2 inhibitors may reduce the production of prostaglandins after infection or injury, thereby reducing inflammation, pain, and fever. In one embodiment, the COX-2 inhibitor may be celecoxib. In alternate embodiments, the COX-2 inhibitor may be amiodipine, valdecoxib, or rofecoxib. A person of ordinary skill will understand that a number of other NSAIDS, including COX-2 inhibitors, may be used separately or in combination with celecoxib in accordance with the present invention.

The pharmaceutical composition may further comprise the GABA analogue, which may have a similar structure to naturally-occurring GABA, thereby enhancing the effects resulting from GABA. In this way, the GABA analogue may decrease activity at the nerve endings to relieve pain by maintaining a proper balance between nerve cell excitation and nerve cell inhibition. Thus, the GABA analogue may further treat nerve and muscle pain due to injury or damage. As one example, the GABA analogue may be pregabalin. In other embodiments, the GABA analogue may be duloxetine, gabapentin, amitriptyline, milnacipran, clomipramine, doxepin, or others.

Finally, the pharmaceutical composition may comprise acetaminophen or another analgesic. A person of ordinary skill in the art will recognize that acetaminophen may elevate the pain threshold, thereby relieving pain, reduce the production of prostaglandins in the brain, thereby reducing inflammation, and reduce fever. Moreover, acetaminophen may also increase the effects of the atypical opioid agonist, such as tramadol. In some embodiments, acetaminophen may be administered in in an amount ranging from 325 mg to 650 mg. In certain preferred embodiments, 500 mg of acetaminophen may be administered.

In one embodiment of the present invention, a method involving the aforementioned pharmaceutical composition may be used to reduce post-operative pain with minimal risk for opioid abuse or addiction. The method may comprise the steps of commencing a surgical procedure involving one or more incision sites; injecting a local surgical anesthesia at the one or more incision sites; completing the surgical procedure; and administering one or more post-operative medications.

Initially, the surgical procedure may involve the one or more incision sites. In particular, this method may apply to a surgery involving one incision site or multiple incision sites. Indeed, a person of ordinary skill in the art will understand that the present invention may be applied to a variety of surgical procedures. As one example, the claimed system, composition and method may be applied to a spinal cord surgery.

At the one or more incision sites, a local surgical anesthesia may be injected. The local surgical anesthesia may comprise ropivacaine, ketorolac, and at least one steroid. In some embodiments, the at least one steroid may be dexamethasone. Once the local surgical anesthesia has been injected, the surgical procedure may be performed and completed. In particular, the surgical procedure may be completed once the aim of the surgery has been accomplished, that is, the bodily tissue or damage thereto has been repaired or replaced.

Once the surgical procedure has been completed, the one or more postoperative medications may be administered. In some embodiments, the postoperative medications may comprise an atypical opioid agonist, an NSAID, a GABA analogue, and acetaminophen. In further embodiments, the atypical opioid agonist may be tramadol, the NSAID may be a COX-2 inhibitor, such as celecoxib, and the GABA analogue may be pregabalin. One of ordinary skill in the art will recognize a number of other compounds may supplant or supplement the aforementioned compounds comprising the postoperative medications.

One or more of the above-disclosed embodiments, in addition to certain alternatives, are provided in further detail below with reference to the attached FIGURES. The disclosed subject matter is not, however, limited to any particular embodiment disclosed.

Advantages

Several advantages of one or more aspects are to provide an anesthetic pharmaceutical composition, system and method that:
(a) reduces intraoperative pain;
(b) delays the onset of postoperative pain;
(c) reduces postoperative pain;
(d) elevates the pain threshold;
(e) counteracts the inflammatory response resulting from damage or infection to bodily tissues; and
(f) decreases the risk of opioid abuse, dependence, or addiction.

These and other advantages of one or more aspects will become apparent from consideration of the ensuing description. Although the description above contains many specifics, these should not be construed as limiting the scope of the embodiments but as merely providing illustrations of some of several embodiments. Thus, the scope of the embodiments should be determined by the claims that are appended and their legal equivalents, rather than by the examples given. The description of the invention which follows should not be construed as limiting the invention to the examples shown and described, because those skilled in the art to which this invention pertains will be able to devise other forms thereof within the ambit of the appended claims.

BRIEF DESCRIPTION OF THE DRAWINGS

FIG. 1 is a flow chart depicting an exemplary anesthetic pharmaceutical method.

The disclosed embodiments may be better understood by referring to the FIGURES in the attached drawings, as provided below. The attached FIGURES are provided as non-limiting examples for providing an enabling description of the method, composition and system claimed. Attention is called to the fact, however, that the appended drawings illustrate only typical embodiments of this invention and are therefore not to be considered as limiting of its scope. One skilled in the art will understand that the invention may be practiced without some of the details included in order to provide a thorough enabling description of such embodiments. Well-known structures and functions have not been shown or described in detail to avoid unnecessarily obscuring the description of the embodiments.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "couple," "coupled," "couples," "coupling," and the like should be broadly understood and refer to connecting two or more elements or signals, electrically, mechanically or otherwise. Two or more electrical elements may be electrically coupled, but not mechanically or otherwise coupled; two or more mechanical elements may be mechanically coupled, but not electrically or otherwise coupled; two or more electrical elements may be mechanically coupled, but not electrically or otherwise coupled. Coupling (whether mechanical, electrical, or otherwise) may be for any length of time, e.g., permanent or semi-permanent or only for an instant.

DETAILED DESCRIPTION

Having summarized various aspects of the present disclosure, reference will now be made in detail to that which is illustrated in the drawings. While the disclosure will be described in connection with these drawings, there is no intent to limit it to the embodiment or embodiments disclosed herein. Rather, the intent is to cover all alternatives, modifications and equivalents included within the spirit and scope of the disclosure as defined by the appended claims.

A pharmaceutical composition, system and method is provided that, in some embodiments, causes analgesia while reducing the risk of opioid abuse or addiction. The composition and system may comprise a cocktail featuring a number of compounds, including those mentioned herein. A person of ordinary skill in the art will recognize that the embodiments discussed herein should not be limited to the specific exemplary compounds provided. Rather, the disclosed compounds may be substituted for or supplemented with different compounds capable of performing the same pain-relieving functions. As one example, the composition and system may comprise at least one intraoperative local injection and at least one post-operative medication.

In accordance with one embodiment, the intraoperative local injection may dull the sensation of pain in a targeted area or region of the body. Alternatively, the intraoperative local injection may alternately numb the entire body. In certain embodiments, the intraoperative local injection may numb intraoperative pain. In other embodiments, the intraoperative local injection may be long-acting and thereby may also relieve postoperative pain. Additionally, the intraoperative local injection may reduce narcotic utilization during the initial time period post-surgery. In yet further embodiments, the intraoperative local injection may relieve pain unrelated to surgery or any medical procedure. Further, the intraoperative local injection may comprise a local anesthetic agent, ketorolac, and at least one steroid.

The local anesthetic agent may comprise a local anesthesia of the amino amide or the amino ester class. In certain exemplary embodiments, the local anesthetic agent may be ropivacaine, which is of the amino amide class. Ropivacaine may inhibit nerve impulse transmission in the targeted tissue for as little as 30 minutes to as long as 12 hours or more. Moreover, ropivacaine may be desirable due to its ability to provide a greater degree of motor sensory differentiation, thereby allowing only the targeted tissue to experience analgesia, while leaving other tissue unaffected.

In alternate embodiments, the local anesthetic agent may comprise another local anesthesia of the amino amide class. For example, bupivacaine, lidocaine, levobupivacaine, or mepivacaine may be included in the local anesthetic agent. In other embodiments, the local anesthetic agent may comprise a local anesthesia of the amino ester class such as tetracaine, procaine, prilocaine, cocaine, chloroprocaine, or benzocaine. Further, the local anesthetic agent may even comprise cinchocaine, benoxinate, proparacaine, or etidocaine. A person of ordinary skill in the art will understand that the local anesthetic agent may comprise one or more of the aforementioned amino amide and amino ester local anesthesia. Indeed, in certain embodiments, the local anesthetic agent may comprise a single compound while, in others, the local anesthetic agent may comprise multiple of the foregoing compounds.

In some embodiments, the intraoperative local injection may also comprise ketorolac. Ketorolac is a nonsteroidal anti-inflammatory drug (NSAID) that may reduce hormones which lead to inflammation and pain in the body. Moreover, ketorolac may provide short-term relief of moderate to severe pain. For example, ketorolac may relieve pain associated with a medical operation or procedure. In other instances, ketorolac may relieve pain that is unrelated to any type of surgery or procedure. One of ordinary skill in the art will recognize that other NSAIDs may be substituted or supplemented. In some embodiments, the NSAID may be naproxen, nabumetone, etodolac, celecoxib, diclofenac, or any combination of the foregoing.

The intraoperative local injection may further comprise at least one steroid. In certain embodiments, the at least one steroid may be dexamethasone, which is an adjuvant agent. In particular, dexamethasone may modify the effects of other pharmacological or immunological compounds, including the local anesthetic agent and the ketorolac of the intraoperative local injection. In addition, dexamethasone may reduce inflammation which may be a result of a surgical operation or not. Further, dexamethasone may extend the duration of the analgesic effects of the intraoperative local injection.

In alternate embodiments, the at least one steroid may comprise a steroid other than dexamethasone. For instance, the at least one steroid may comprise dexmedetomidine. One of ordinary skill in the art will understand that other steroids may be substituted or supplemented for dexamethasone or dexmedetomidine. Moreover, in some embodiments, the intraoperative local injection may comprise more than one steroid. In other embodiments, the intraoperative local injection may comprise only one steroid.

The at least one postoperative medication may comprise an atypical opioid agonist, a non-steroidal anti-inflammatory drug, a gamma-aminobutyric (GABA) analogue, and acetaminophen. The atypical opioid agonist may mimic the effects of endogenous opioids by binding to opioid receptors, thereby decreasing the body's ability to sense pain. However, the atypical opioid agonist causes less opioid receptor activation than full opioid agonists, such as hydrocodone, oxycodone, methadone, fentanyl, codeine, and morphine. Due to the reduced receptor activation, the atypical opioid agonist may be less potent than full opioid agonists. In this manner, the atypical opioid agonist may have a reduced tendency to result in overuse, dependency, addiction, or overdose.

In addition to the foregoing effects, the atypical opioid agonist may cause presynaptic release of serotonin and norepinephrine in the brain and also inhibit reuptake of the same. In some embodiments, the effect may be antinociception. Additionally, the effect may also be reduction of the emotional sensation of pain, due to the pivotal role serotonin and norepinephrine play in the emotional pain experience.

The atypical opioid agonist may preferably comprise tramadol. In other embodiments, the atypical opioid agonist may comprise buprenorphine, butorphanol, or pentazocine. In still alternate embodiments, the atypical opioid agonist may comprise a full opioid agonist. In such embodiments, the full opioid agonist may be fentanyl, codeine, hydrocodone, oxycodone, morphine, or methadone. The atypical opioid agonist may, in some embodiments, comprise only one of the foregoing opioid agonists, and in others, more than one of the foregoing.

In certain embodiments, the postoperative medication may comprise the non-steroidal anti-inflammatory drug (NSAID). In some embodiments, the NSAID is a cyclooxygenase-2 (COX-2) inhibitor. A person of ordinary skill in the art will recognize that the COX-2 inhibitor may block COX-2 enzymes, which, in response to surgery, infection, or other injury, produce prostaglandins. Prostaglandins, in turn, regulate inflammation so by inhibiting COX-2 enzymes, and thereby production of prostaglandins, inflammation and pain is relieved.

Moreover, the COX-2 inhibitor may be celecoxib. In some embodiments, celecoxib may be substituted or supplemented with other COX-2 inhibitors. In these embodiments, the other COX-2 inhibitors may be amiodipine, valdecoxib, or rofecoxib. Alternatively, the NSAID may be a compound other than a COX-2 inhibitor, which nonetheless serves to block the inflammatory response due to infection or injury. For example, the NSAID may be a COX-1 inhibitor. In still other embodiments, the NSAID may be a combination of COX-2 inhibitors and other NSAID compounds, such as COX-1 inhibitors.

According to some embodiments of the present invention, the GABA analogue may have a similar structure to endogenous GABA. In this manner, the GABA analogue may serve to mimic and enhance the effects of naturally-occurring GABA. More particularly, during surgery or other medical procedures, nerve cells fire more than usual resulting in an excitatory state. This excitatory state results, in part, in a lower tolerance for pain. The GABA analogue may target this issue by maintaining a proper balance between nerve cell excitation and inhibition. Further, the GABA analogue may decrease activity at the nerve endings and, in turn, relieve pain felt at those nerves. In effect, the GABA analogue may calm the nervous system.

In certain embodiments, the GABA analogue may be pregabalin. Pregabalin may be desirable because of its ability to treat nerve and muscle pain. More particularly, pregabalin may decrease activity at the nerve endings, thereby relieving pain. In one embodiment, pregabalin may mitigate pain due to spinal cord injury or nerve damage. Additionally, pregabalin may have a low risk for abuse or dependence. In other embodiments, the GABA analogue may be duloxetine, gabapentin, amitriptyline, milnacipran, clomipramine, doxepin, vigabatrin, imipramine, or acamprosate. A person of ordinary skill in the art will understand and appreciate that other GABA analogues may be included in accordance with this invention.

Finally, the at least one postoperative medication may comprise an analgesic, such as acetaminophen. Acetaminophen may act as an anti-inflammatory agent by reducing inflammation and fever associated therewith. In addition, acetaminophen may elevate the pain threshold. In this way, acetaminophen may relieve pain. Further, acetaminophen may be desirable because it may increase the effects of the atypical opioid agonist.

With reference to FIG. 1, one embodiment of the present invention may involve a method of delivering the aforementioned pharmaceutical composition. FIG. 1 illustrates a flowchart of one embodiment of the method of this invention. The method may effectively reduce postoperative, or other, pain. Additionally, the method may provide a lessened risk for opioid abuse, dependence, or addiction. In certain embodiments, including that demonstrated in FIG. 1, the method may comprise the steps of commencing a surgical procedure involving one or more incision sites (block 101); injecting an intraoperative local injection (block 102); performing and completing the surgical procedure (block 103); and administering one or more postoperative medications (block 104).

More specifically, the surgical procedure may first be commenced (block 101). The surgical procedure may involve the one or more incision sites. In some embodiments, the surgical procedure may involve a single incision site. In alternate embodiments, the surgical procedure may involve two, or even more, incision sites. In certain embodiments, the surgical procedure may be commenced by cutting through the skin of a patient at the one or more incision sites. One of ordinary skill in the art will recognize that the surgical procedure may be virtually any type of surgical procedure, including medically-necessary, medically-beneficial, cosmetic, or otherwise. In some exemplary embodiments, the surgical procedure may involve the spinal cord.

After the surgical procedure has been commenced, the intraoperative local injection may be injected at the one or more incision sites (block 102). In particular, in embodiments where there is exactly one incision site, the intraoperative local injection may be injected at that incision site. On the other hand, in embodiments where there is more than one incision site, the intraoperative local injection may be applied to each of the multiple incision sites. As discussed in greater detail above, the intraoperative local injection may comprise a local anesthetic agent, an NSAID, and at least one steroid. In further embodiments, the local anesthetic agent may be ropivacaine, the NSAID may be ketorolac, and the at least one steroid may be dexamethasone.

The amount of intraoperative local injection may depend on the size and quantity of the one or more incision sites. In embodiments wherein the one or more incision sites are relatively larger, a greater amount of the intraoperative local injection may be injected. Oppositely, in embodiments wherein the one or more incision sites are relatively smaller, a lesser amount of the intraoperative local injection may be injected. For example, the local anesthetic agent, such as ropivacaine, may be injected in an amount ranging from 12 mL to 20 mL. Also, the NSAID, such as ketorolac, may be injected in an amount ranging from 1 mL to 2 mL. Further, the at least one steroid, such as dexamethasone, may be injected in an amount ranging from 1 mL to 3 mL. The intraoperative local injection may be injected in greater or lesser amounts, depending on the type of surgery and size of the one or more incision sites. One of ordinary skill will understand that the foregoing ranges are provided by way of example, and not limitation.

In certain embodiments, after the intraoperative local injection has been injected at the one or more incision sites, the surgical procedure may immediately thereafter be performed and then, completed (block 103). In other embodiments, after the intraoperative local injection has been injected, the method may comprise waiting a specified period of time and then, performing and completing the surgical procedure. One of ordinary skill in the art will appreciate that completion of the surgical procedure may be defined by the overall goal of the surgical procedure. For example, in embodiments wherein the surgical procedure involves setting a broken bone, the surgical procedure may be completed once the broken bone has been set in the proper position. Again, as discussed above, the surgical procedure may comprise enumerable types of surgeries, operations, and other medical procedures. Further, one of ordinary skill will recognize that the intraoperative local injection may be injected at the one or more incision sites (block 102) prior to the surgery being performed (block 103) or, in other embodiments, after the surgery has been performed and completed (block 103).

After the surgical procedure has been completed, the one or more postoperative medications may be administered (block 104). The postoperative medications may be administered orally. In such embodiments, the postoperative medications may be in solid (i.e., a pill) or liquid form. In alternate embodiments, the postoperative medications may variously be administered transdermally, intravenously, perineurally, sublingually, or transcutaneously. Furthermore, in certain embodiments, the postoperative medications may be administered together or separately. Even further, the postoperative medications may be administered separately, but sequentially, or separately, at various times of the day or night.

The one or more postoperative medications may comprise an atypical opioid agonist, an NSAID, a GABA analogue, and acetaminophen, as discussed in more detail above. More specifically, the atypical opioid agonist, in some embodiments, may comprise tramadol. The NSAID may comprise a cyclooxygenase-2 inhibitor, such as celecoxib. In addition, the GABA analogue may comprise pregabalin. Moreover, one of ordinary skill in the art will understand that while acetaminophen may be preferable, other analgesics may be substituted or supplemented in accordance with this invention. Finally, the one or more postoperative medications may comprise additional or other substituted compounds.

It should be emphasized that the above-described embodiments are merely examples of possible implementations. Many variations and modifications may be made to the above-described embodiments without departing from the principles of the present disclosure. All such modifications and variations are intended to be included herein within the scope of this disclosure and protected by the following claims.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

CONCLUSIONS, RAMIFICATIONS, AND SCOPE

While certain embodiments of the invention have been illustrated and described, various modifications are contemplated and can be made without departing from the spirit and scope of the invention. For example, the intraoperative local injection may comprise additional or different compounds which serve the overall purpose of analgesia, anti-inflammation, and anti-opioid dependence. As another example, the sequence of the steps of the method may be varied.

Accordingly, it is intended that the invention not be limited, except as by the appended claim(s).

The teachings disclosed herein may be applied to other systems, and may not necessarily be limited to any described herein. The elements and acts of the various embodiments described above can be combined to provide further embodiments. All of the above patents and applications and other references, including any that may be listed in accompanying filing papers, are incorporated herein by reference. Aspects of the invention can be modified, if necessary, to employ the systems, functions and concepts of the various references described above to provide yet further embodiments of the invention.

Particular terminology used when describing certain features or aspects of the invention should not be taken to imply that the terminology is being refined herein to be restricted to any specific characteristics, features, or aspects of the anesthetic pharmaceutical composition, system, and method with which that terminology is associated. In general, the terms used in the following claims should not be constructed to limit the anesthetic pharmaceutical composition, system, and method to the specific embodiments disclosed in the specification unless the above description section explicitly define such terms. Accordingly, the actual scope encompasses not only the disclosed embodiments, but also all equivalent ways of practicing or implementing the disclosed system, method and apparatus. The above description of embodiments of the anesthetic pharmaceutical composition, system, and method is not intended to be exhaustive or limited to the precise form disclosed above or to a particular field of usage.

While specific embodiments of, and examples for, the method, system, and apparatus are described above for illustrative purposes, various equivalent modifications are possible for which those skilled in the relevant art will recognize.

While certain aspects of the method and system disclosed are presented below in particular claim forms, various aspects of the method, system, and apparatus are contemplated in any number of claim forms. Thus, the inventor reserves the right to add additional claims after filing the application to pursue such additional claim forms for other aspects of the anesthetic pharmaceutical composition, system, and method.

What is claimed is:

1. A pharmaceutical composition for use in the treatment of surgical pain and discomfort, comprising
    an intraoperative local injection;
    an atypical opioid agonist;
    a non-steroidal anti-inflammatory drug;
    a gamma-aminobutyric acid analogue; and
    acetaminophen.
2. The pharmaceutical composition of claim 1, wherein the intraoperative local injection is long-acting and further comprises
    at least one local anesthetic agent;
    ketorolac; and
    at least one steroid.
3. The pharmaceutical composition of claim 2, wherein the at least one local anesthetic agent comprises ropivacaine.
4. The pharmaceutical composition of claim 2, wherein the at least one steroid is dexamethasone.
5. The pharmaceutical composition of claim 1, wherein the atypical opioid agonist is tramadol.
6. The pharmaceutical composition of claim 1, wherein the non-steroidal anti-inflammatory drug is a cyclooxygenase-2 inhibitor.
7. The pharmaceutical composition of claim 6, wherein the non-steroidal anti-inflammatory drug is celecoxib.
8. The pharmaceutical composition of claim 1, wherein the gamma-aminobutyric acid analogue is pregabalin.

* * * * *